(12) United States Patent
Ng

(10) Patent No.: US 11,786,228 B2
(45) Date of Patent: Oct. 17, 2023

(54) MULTI-USE TONGUE DEPRESSOR INSTRUMENT AND METHOD OF USE

(71) Applicant: Wai Pong Ng, Albuquerque, NM (US)

(72) Inventor: Wai Pong Ng, Albuquerque, NM (US)

( * ) Notice: Subject to any disclaimer, the term of this patent is extended or adjusted under 35 U.S.C. 154(b) by 879 days.

(21) Appl. No.: 16/671,646

(22) Filed: Nov. 1, 2019

(65) Prior Publication Data

US 2021/0128127 A1    May 6, 2021

(51) Int. Cl.
*A61B 13/00* (2006.01)

(52) U.S. Cl.
CPC ..................... *A61B 13/00* (2013.01)

(58) Field of Classification Search
CPC ........... A61B 13/00; A61B 1/24; A61B 5/682; A61B 17/244
See application file for complete search history.

(56) References Cited

U.S. PATENT DOCUMENTS

| | | | | | |
|---|---|---|---|---|---|
| 1,510,304 | A | * | 9/1924 | Cameron | A61B 1/0676 600/241 |
| 2,690,745 | A | * | 10/1954 | Govan | A61B 1/24 D24/136 |
| 3,760,798 | A | * | 9/1973 | Edinger | A61B 1/0669 600/241 |
| 3,867,927 | A | * | 2/1975 | Hergott | A61B 5/107 600/203 |
| 3,900,924 | A | * | 8/1975 | Meltzner | A61B 1/24 24/339 |
| 3,916,881 | A | * | 11/1975 | Heine | A61B 1/0669 600/212 |
| D371,310 | S | * | 7/1996 | Ekeoba | D10/71 |
| 5,913,586 | A | * | 6/1999 | Marshall | G01B 3/004 33/759 |
| D574,494 | S | * | 8/2008 | Schmitt | D24/136 |
| D615,889 | S | * | 5/2010 | Cluff | D10/74 |
| 2006/0143934 | A1 | * | 7/2006 | Perry | G09B 23/04 33/494 |
| 2007/0204476 | A1 | * | 9/2007 | Brothers | B26B 29/06 33/483 |
| 2008/0172896 | A1 | * | 7/2008 | Frantellizzi | G01B 3/04 451/523 |
| 2010/0229412 | A1 | * | 9/2010 | Kenney | A61B 5/1072 33/512 |

(Continued)

FOREIGN PATENT DOCUMENTS

CA    2738921 A1 * 10/2012    ............. A61B 13/00

OTHER PUBLICATIONS

English translation of CA 2738921, machine translated by espacenet.com, translated on Aug. 9, 2022.*

*Primary Examiner* — Tu A Vo
(74) *Attorney, Agent, or Firm* — Alberto A. León; ALEONLAW, P.C.

(57) ABSTRACT

A multi-use tongue depressor fabricated using the same materials and dimensions as commercially available ones. The tongue depressor depresses, retracts, move, shifts or sweeps a patient's tongue during a healthcare provider's examination of the patient's oral cavity in such a way as to maximize visibility of a target pathology inside the patient's oral cavity, the tongue depressor is adapted to conduct distance, depth and position measurements in the patient's oral cavity so as to assist health care providers in the identification and treatment of oral pathologies.

2 Claims, 3 Drawing Sheets

(56) References Cited

U.S. PATENT DOCUMENTS

2015/0082644 A1* 3/2015 Cromwell ............. G01B 3/006
　　　　　　　　　　　　　　　　　　　　　　　33/492
2019/0254502 A1* 8/2019 Holland ............. A61B 1/00039

* cited by examiner

MULTI-USE TONGUE DEPRESSOR INSTRUMENT AND METHOD OF USE

CROSS-REFERENCE TO RELATED APPLICATION

Non-Applicable

STATEMENT REGARDING FEDERALLY SPONSORED RESEARCH AND DEVELOPMENT

Non-applicable

THE NAMES OF THE PARTIES TO A JOINT RESEARCH AGREEMENT

Non-applicable

INCORPORATION-BY-REFERENCE OF MATERIAL SUBMITTED ON A COMPACT DISC

Non-applicable

BACKGROUND OF THE INVENTION

Technical Field of the Invention

The present invention relates generally to medical instruments, more particularly to medical instruments to facilitate the inspection of the oral cavity, and still more particularly to an instrument that facilitates the examination and inspection of the human oral cavity while allowing measuring the exact size of an oral pathological lesion, pathology or deformity, and its relative position with respect to a patient's teeth or gums.

Description of the Related Art Including Information Disclosed Under 37 CFR 1.97 and 37 CFR 1.98

The following description of the art related to the present invention refers to a number of publications and references. Discussion of such publications and references herein is given to provide a more complete background of the principles related to the present invention and is not to be construed as an admission that such publications are necessarily prior art for patentability determination purposes.

Tongue depressors are instruments that many healthcare providers including, but not limited to, doctors, dentists, nurse practitioners and nurses commonly use to press down a patient's tongue. The main goal when using a tongue depressor is to allow better visualization of the oral cavity, throat or pharynx. Specifically, tongue depressors allow the examining health care provider to sweep and retract tissue to obtain a clearer and more expansive view thus facilitating the dental and/or medical evaluation of the oral cavity, throat or pharynx.

Typically, tongue depressors are thin blades comprising a broad flat extremity that provides sufficient contact surface to effectively press down or sweep the tongue, thus facilitating the medical or dental examination of the oral cavity and surrounding structures by exposing them to visual inspection. Tongue depressors are usually made out of wood or metal and are shaped like a spatula smoothed and rounded at both ends.

In the field of dentistry, more particularly, maxillofacial surgery, it is important to clearly visualize an oral pathological lesion such as an ulcer, growth, defect or trauma. Maxillofacial surgery practitioners commonly use tongue depressors to depress, retract or sweep the patient's tongue to facilitate that visualization.

There is another component, however, of an effective examination of an oral pathological lesion. A healthcare provider conducting such an examination, especially if the possibility of a curative or surgical procedure is being contemplated, also needs to be able to measure the target lesion to allow proper documentation and to facilitate such subsequent procedures.

BRIEF SUMMARY OF THE INVENTION

Objects, advantages and novel features, and further scope of applicability of the present invention will be set forth in part in the detailed description to follow, taken in conjunction with the accompanying drawings. The objects, advantages and novel features, and further scope of applicability of the present invention will become apparent to those skilled in the art upon examination of the following, or may be learned by practice of the invention. The objects and advantages of the invention may be realized and attained by means of the instrumentalities and combinations particularly pointed out in the appended claims.

Tongue depressors have been known and widely used in the fields of medicine, dentistry and maxillofacial surgery to facilitate oral examinations for many years. The modern and most widely used tongue depressor is made out of wood and is disposable and used for a single-patient examination.

A principal object the new and useful invention embodied in the present application is to provide a multi-use tongue depressor comprising a substantially flat upper horizontal surface and a corresponding substantially flat under horizontal surface. The main embodiment of the present invention comprises a tongue depressor fabricated using the same materials and dimensions as commercially available ones. Alternative embodiments of the present invention comprise tongue depressors fabricated using hard plastic, stainless steel, ceramic composites and other materials that can be sterilized for multiple uses.

The tongue depressor of the present invention comprises an upper horizontal surface and an under horizontal surface. The upper surface of the tongue depressor of the present invention comprise two lateral edges and a centerline. The upper surface further comprising printed dimensional markings, akin to a ruler, clearly visible to the eye and printed or etched along both lateral edges, and on the centerline. The markings comprise dimensions in any available measuring scale such as millimeters, centimeters or inches scaled in increasing numbers starting on the front end and continuing ascendingly.

The markings located on along the lateral edges of the upper surface of the tongue depressor of the present invention allow and facilitate measuring the size of a target lesion and the relative location of a target lesion(s) linearly (top or bottom) using a reference point in the patient's mouth. The markings located on the centerline of the upper surface allow and facilitate the measurement of the depth (center) of a lesion(s) using a reference point in the patient's mouth.

BRIEF DESCRIPTION OF THE DRAWINGS

The embodiments of the present invention will be further described in detail hereinafter with reference to the drawings, wherein.

DETAILED DESCRIPTION OF THE INVENTION

Figure 1:
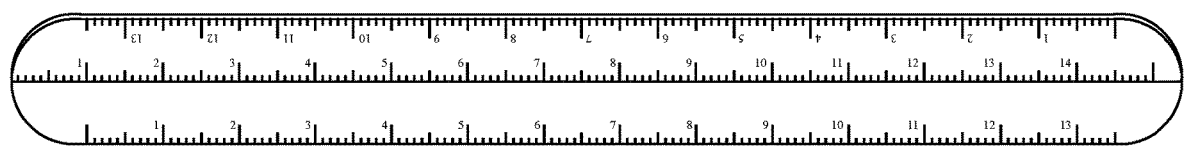
FIG. 1: a top view of the upper surface of the tongue depressor of the present invention illustrating three markings' lines; one at each edge and a third one at the centerline position. Wooden tongue depressor (standard size 16 mm×150 mm).

In the main embodiment of the invention, the tongue depressor is a standard wooden one, with the markings being black, as illustrated in FIG. 1, or colored so as to create a contrast with respect to the blade's color, thus maximize visibility, and further being permanently applied to the upper surface of the tongue depressor during fabrication.

In the embodiment comprising a wooden tongue depressor, methods available to print on wooden surfaces such as woodcut, etching, pressing, engraving, stenciling or direct printing are used.

Woodcut, etching, pressing, engraving and stenciling usually require an additional printing and/or inking step. For obvious reasons, any ink or printing materials used would have to be non-toxic and susceptible to sterilization without losing the quality of the print.

Another process useful to achieve the marks on the upper surface of the tongue depressor would be to affix a pre-fabricated sticker already comprising the marks to the upper surface of the tongue depressor.

In an alternative embodiment of the present invention, the tongue depressor can be fabricated using a variety of non-toxic medical grade materials such as medical polymers (e.g., thermo-plastics) or stainless steel. Those embodiments require that a pre-fabricated sticker comprising the marks be affixed to the tongue depressor during fabrication.

Another embodiment of the present invention comprises an upper surface further comprising a front end and a back end, the front end comprising illuminating means such as those known in the prior art (See, e.g., U.S. Pat. Nos. 4,807,599 and 5,318,009 to Robinson).

The main object of the present invention is to provide a tongue depressor instrument useful to visualize the position of the target of an oral examination, i.e., an oral lesion(s) such as a growth, defect or trauma. That object is accomplished by using the tongue depressor to depress, retract, move, shift or sweep the patient's tongue in such a way as to maximize visibility of a target area inside the oral cavity.

Figure 2:
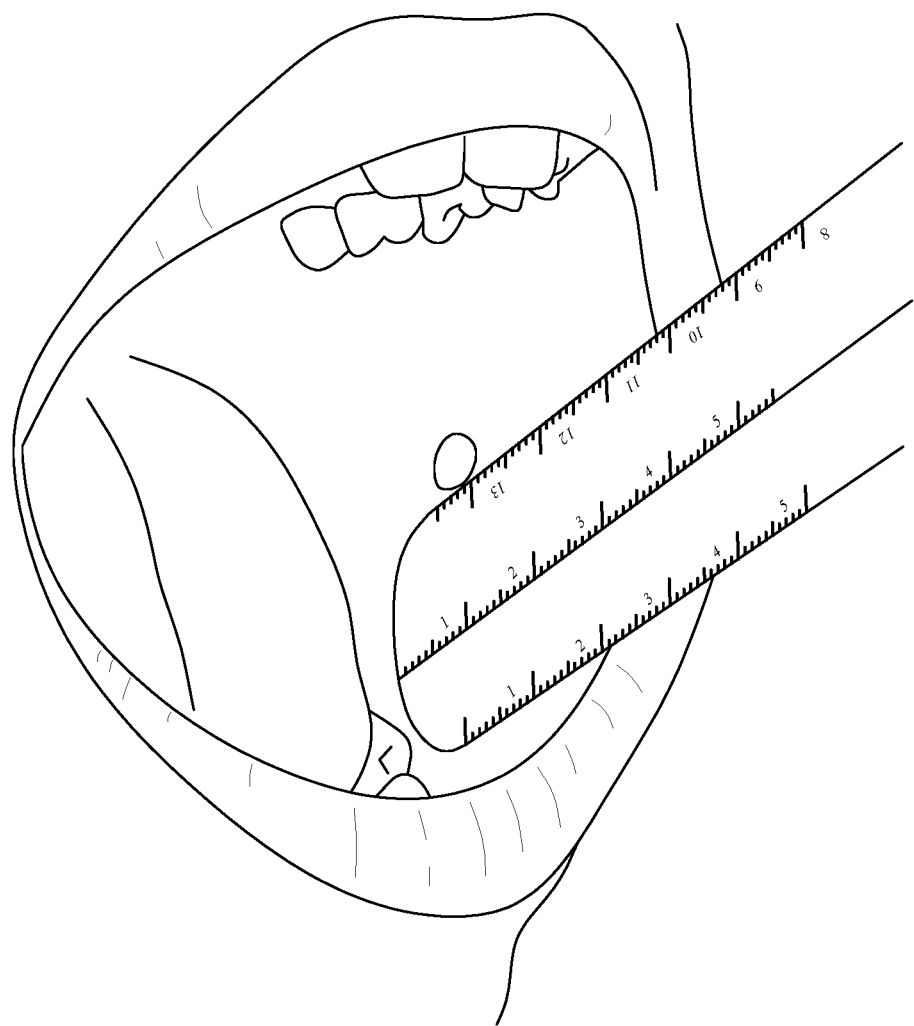
FIG. 2: a perspective view of the tongue depressor of the present invention being used in a patient's mouth.
Figure 3:
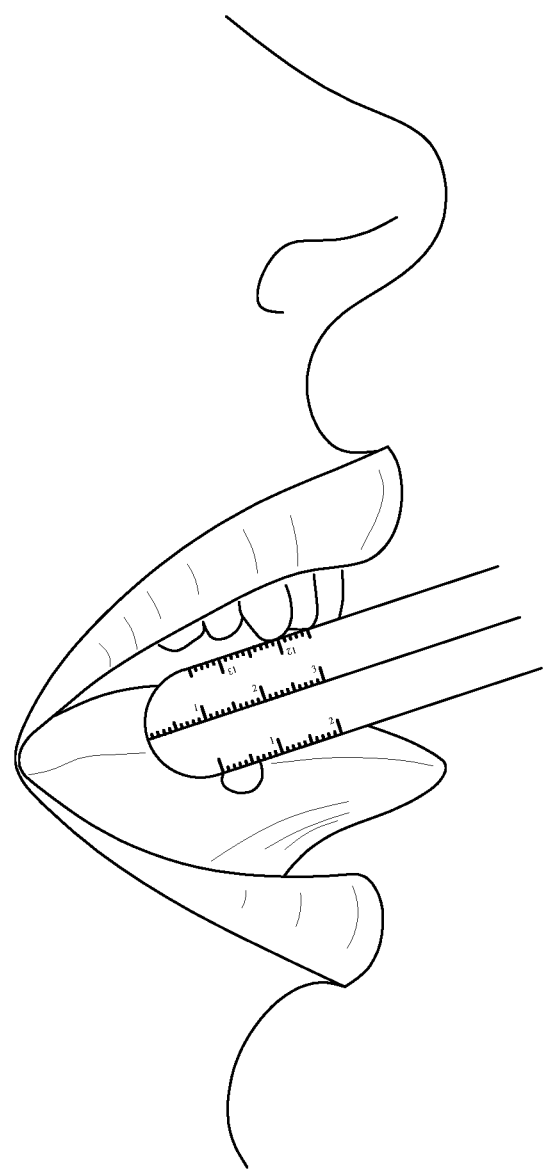
FIG. 3: an exploded view of the tongue depressor of the present invention being used in a patient's mouth showing it making an example measurement between a lesion area and a pre-determined, pre-measured point of reference.

Another object of the present invention is to provide a tongue depressor instrument that also allows the user to measure the target area's dimensions. FIG. 2 and FIG. 3 illustrate the tongue depressor of the present invention being used to visualize the position of a lesion (one on the patient's cheek and the other on the patient's tongue), to measure the target area's dimensions, and to determine the lesion's position relative to other structures or markers in the patient's mouth. Still another object of the present invention is to provide a tongue depressor instrument that further allows the user to accurately document the dimensions and position (relative to other oral structures) of the target area(s) of the examination.

During oral examination using the tongue depressors of the prior art, the healthcare provider conducting the examination often visualizes and estimates the target or affected areas such as lesions, resulting in inaccurate documentation. Moreover, examinations of oral lesions usually require the healthcare provider to fetch an additional measuring device and conduct a second examination.

The present invention saves time, reduced the number of instruments used in oral examinations targeting lesions and improve the accuracy of visualizing and measuring the lesion and documenting its size and location in the healthcare provider's notes. That documentation becomes crucial for the purposes of diagnosing a medical condition related to the lesion(s), designing the appropriate treatment or any necessary any follow-up examination and or surgical procedure that might be necessary.

Obtaining the measurements and exact location of an oral lesion or affected area (growth, deformity, abnormality, etc.) allows the healthcare practitioner to accurately describe the lesion(s) in its notes for the purposes of, for example, referring the patient to a specialist or simply to be able to recall the lesion(s) characteristics at a later date. Further, the measurement of a patient's anatomical structures and characteristics greatly aids a healthcare provider's treatment planning of dental or surgical procedures to treat conditions including, but not limited to oral pathologies, skeletal deformities and dental defects.

The present invention is also useful in the dental and periodontal care fields because it aids the healthcare provider to obtain measurements that facilitate the often-necessary dental, specifically periodontal, description of teeth, dental relationships, range of motion of jaw and the general anatomy of the oral cavity.

What I claim is:

1. A multi-use tongue depressor wherein the tongue depressor is fabricated using a material comprising wood, polymer material, hard plastic, stainless steel, or ceramic composites, the tongue depressor being used to depress, retract, move, shift or sweep a patient's tongue during a healthcare provider's examination of the patient's oral cavity to maximize visibility of a target pathology inside the patient's oral cavity, the tongue depressor being adapted to conduct distance, depth and position measurements in the patient's oral cavity so as to assist health care providers to identify and treat oral pathologies, the tongue depressor comprising:
   a) substantially flat elongated blade comprising a front end, a back end, an upper horizontal surface, an under horizontal surface, two longitudinal lateral edges running along the surfaces and a centerline running along the center of the upper horizontal surface; and
   b) multiple dimensional markings comprising millimeters, centimeters, or inches dimensions, wherein a first set of the multiple dimensional markings is printed or etched in increasing numbers starting on the front end and continuing ascendingly along a first lateral edge of the lateral edges, a second set of the multiple dimensional markings is printed or etched in decreasing numbers starting on the front end and continuing descendingly along a second lateral edge of the lateral edges, and a third set of the multiple dimensional markings is printed or etched in increasing numbers starting on the front end and continuing ascendingly in a middle portion of the upper horizontal surface between the first set of the multiple dimensional markings and the second set of the multiple dimensional markings and along the centerline, the multiple dimensional markings allowing and facilitating measuring a size of the target pathology in the patient's oral cavity and a relative location of the target pathology linearly, top or bottom, using a known reference point in the patient's mouth, the reference point being a fixed marker in the patients oral cavity such as a tooth, with the third set of dimensional markings located on the centerline of the upper horizontal surface scaled in increasing numbers starting on the front end and continuing ascendingly thus allowing and facilitating the measurement of the depth or center of the target pathology relative to the known reference point in the patient's oral cavity, and with the first and second set of dimensional markings located on along the lateral edges of the upper horizontal surface allowing and facilitating measuring the size of the target pathology and the relative location of the target pathology linearly, top or bottom, relative to the reference point in the patient's oral cavity, and with the multiple dimensional markings being black or colored so as to create a contrast with respect to the blade's color, thus maximizing visibility of said multiple dimensional markings.

2. The tongue depressor of claim 1, wherein the polymer material comprising a thermoplastic, disposable plastic, or recyclable plastic.

* * * * *